US010699592B2

(12) United States Patent
Kochura et al.

(10) Patent No.: US 10,699,592 B2
(45) Date of Patent: Jun. 30, 2020

(54) SYSTEM AND METHOD FOR ASSESSING READING SKILLS

(71) Applicant: International Business Machines Corporation, Armonk, NY (US)

(72) Inventors: Nadiya Kochura, Bolton, MA (US); Fang Lu, Billerica, MA (US)

(73) Assignee: International Business Machines Corporation, Armonk, NY (US)

( * ) Notice: Subject to any disclaimer, the term of this patent is extended or adjusted under 35 U.S.C. 154(b) by 201 days.

(21) Appl. No.: 15/282,466

(22) Filed: Sep. 30, 2016

(65) Prior Publication Data

US 2018/0096626 A1    Apr. 5, 2018

(51) Int. Cl.
| G09B 5/00 | (2006.01) |
| G09B 17/00 | (2006.01) |
| G09B 5/02 | (2006.01) |
| G09B 5/12 | (2006.01) |
| G09B 7/02 | (2006.01) |
| A61B 5/024 | (2006.01) |
| A61B 5/00 | (2006.01) |

(Continued)

(52) U.S. Cl.
CPC .............. *G09B 17/003* (2013.01); *G09B 5/02* (2013.01); *G09B 5/12* (2013.01); *G09B 7/02* (2013.01); *A61B 5/024* (2013.01); *A61B 5/0533* (2013.01); *A61B 5/168* (2013.01); *A61B 5/4088* (2013.01); *A61B 5/4266* (2013.01); *A61B 5/7264* (2013.01); *A61B 5/7267* (2013.01)

(58) Field of Classification Search
CPC ......... G09B 5/02; G09B 17/003; G06F 17/27; G06F 17/274
See application file for complete search history.

(56) References Cited

U.S. PATENT DOCUMENTS

| 4,332,566 A | * 6/1982 | Mazeski | .............. A61B 5/0476 434/178 |
| 7,069,508 B1 | 6/2006 | Bever | |

(Continued)

OTHER PUBLICATIONS

Dehaene et al., "Illiterate to literate: behavioural and cerebral changes induced by reading acquisition," Nature Reviews Neuroscience, AOP, published online Mar. 18, 2015; doi: 10-1038/nrn3924.

(Continued)

*Primary Examiner* — Peter R Egloff
(74) *Attorney, Agent, or Firm* — Pepper Hamilton LLP

(57) ABSTRACT

Embodiments can provide a computer implemented method in a data processing system comprising a processor and a memory comprising instructions which are executed by the processor to cause the processor to implement a reading skill assessment system, the method comprising: processing a body of text; applying one or more text mutators to the body of text to produce a mutated text output; presenting the mutated text output to a reader; prompting the reader to provide one or more answers to one or more questions regarding the mutated text output; processing the one or more answers provided by the reader; processing one or more metrics collected from the reader; calculating a reader skill score for the reader; mapping the calculated reader skill score against one or more baseline reading skill score levels; and suggesting a reading skill level to the reader.

15 Claims, 6 Drawing Sheets

(51) Int. Cl.
*A61B 5/16* (2006.01)
*A61B 5/053* (2006.01)

(56) References Cited

U.S. PATENT DOCUMENTS

| | | | |
|---|---|---|---|
| 8,517,739 B2 | 8/2013 | Dekkers | |
| 9,875,669 B2* | 1/2018 | Nielson | A61B 5/162 |
| 2003/0068603 A1* | 4/2003 | Cupp | G09B 17/00 |
| | | | 434/178 |
| 2004/0049391 A1 | 3/2004 | Polyanyi et al. | |
| 2004/0067472 A1 | 4/2004 | Polyanyi et al. | |
| 2006/0166174 A1* | 7/2006 | Rowe | G09B 5/06 |
| | | | 434/236 |
| 2007/0011005 A1* | 1/2007 | Morrison | G09B 5/06 |
| | | | 704/231 |
| 2007/0202474 A1* | 8/2007 | Miller | G09B 17/04 |
| | | | 434/156 |
| 2008/0059145 A1 | 3/2008 | Wood et al. | |
| 2011/0076654 A1 | 3/2011 | Green et al. | |
| 2014/0127667 A1 | 5/2014 | Iannacone | |
| 2014/0255898 A1 | 9/2014 | Burge et al. | |
| 2015/0118661 A1* | 4/2015 | Haruta | G09B 5/00 |
| | | | 434/169 |
| 2015/0221227 A1 | 8/2015 | Berger et al. | |
| 2016/0125753 A1* | 5/2016 | Telep | G09B 17/006 |
| | | | 704/9 |

OTHER PUBLICATIONS

Mano et al. "The Role of Left Occipitotemporal Cortex in Reading: Reconciling Stimulus, Task, and Lexicality Effects," Cerebral Cortex, Oxford University Press, 2012; doi: 10.1093/cercor.bhs093.
Cohen et al., "Reading normal and degraded words: Contribution of the dorsal and ventral visual pathways," Neuroimage 40 (2008), pp. 353-366; doi: 10.1016/j.neuroimage.2007.11.036.
Non-Final Office Action dated Jun. 4, 2018 in corresponding U.S. Appl. No. 15/282,458.
Final Office Action dated Dec. 5, 2018 in corresponding U.S. Appl. No. 15/282,458.
U.S. Appl. No. 15/282,458, filed Sep. 30, 2016, 2018/0096625 A1.

* cited by examiner

SYSTEM AND METHOD FOR ASSESSING READING SKILLS

TECHNICAL FIELD

The present application relates generally to a system and method that can be used to assess reading skills.

BACKGROUND

Existing reading evaluation systems rely on pre-built test data, which are created for people with cognitive impairments that affect reading. However, the diagnosis of these cognitive impairments is assumed. Moreover, existing reading evaluation systems lack personalization and the ability to adapt to a particular person's needs. What is needed is an accurate method to estimate a person's reading skill level while accounting for any possible cognitive impairment without underlying assumptions, and providing personalized recommendations to that person.

SUMMARY

Embodiments can provide a computer implemented method, in a data processing system comprising a processor and a memory comprising instructions which are executed by the processor to cause the processor to implement a reading skill assessment system, the method comprising: processing a body of text; applying one or more text mutators to the body of text to produce a mutated text output; presenting the mutated text output to a reader; prompting the reader to provide one or more answers to one or more questions regarding the mutated text output; processing the one or more answers provided by the reader; processing one or more metrics collected from the reader; calculating a reader skill score for the reader; mapping the calculated reader skill score against one or more baseline reading skill score levels; and suggesting a reading skill level to the reader.

Embodiments can further provide a method further comprising applying one or more text mutators to the body of text to produce a mutated text output, wherein the text mutators comprise at least one of: pseudoword injections, letter transposition injections, randomizing text, word rotation, mirroring, letter spacing, word extraction, and text stretching.

Embodiments can further provide a method further comprising jumbling one or more letters of text; not producing existent words; producing only short words; transposing one or more letters of text; and splitting words.

Embodiments can further provide a method further comprising processing one or more metrics collected from the reader, wherein the metrics collected comprise at least one of: mean reading duration per word, reading speed, total reading time, correctness of responses regarding text understanding, time needed to provide responses, biometrics, word reading level with applied text mutators, and sentence reading level with applied mutators.

Embodiments can further provide a method further comprising determining whether the reader had difficulty reading the mutated text output based upon the one or more answers received and one or more metrics collected; if the reader had difficulty reading the mutated text output: applying an alternate set of text mutators to produce an alternate mutated text output; presenting the alternate mutated text output to a reader; prompting the reader to provide one or more answers to one or more questions regarding the alternate mutated text output; processing the one or more answers provided by the reader; processing one or more metrics collected from the reader; calculating a reader skill score for the reader; and mapping the calculated reader skill score against one or more baseline reading skill score levels.

Embodiments can further provide a method further comprising transforming one or more subsequent text documents into a format suitable for the reader's suggested reading skill level by applying one or more of the text mutators to the subsequent text documents.

Embodiments can further provide a method further comprising deriving the one or more baseline reading skill score levels by: creating the one or more sets of parameterized text mutators for one or more different reading skill levels; applying a reading skill score function to calculate baseline scores for one or more tested reading skill levels; adjusting the reading skill score function to best match with the one or more tested reading skill levels; optimizing the parameters of the one or more sets of text mutators; creating the one or more baseline reading skill score levels for each of the one or more tested reading skill levels; and associating one or more sets of text mutators with the one or more tested reading skill levels.

In another illustrative embodiment, a computer program product comprising a computer usable or readable medium having a computer readable program is provided. The computer readable program, when executed on a processor, causes the processor to perform various ones of, and combinations of, the operations outlined above with regard to the method illustrative embodiment.

In yet another illustrative embodiment, a system is provided. The system may comprise a reading skill assessment processor configured to perform various ones of, and combinations of, the operations outlined above with regard to the method illustrative embodiment.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF EXEMPLARY EMBODIMENTS

Figure 1:
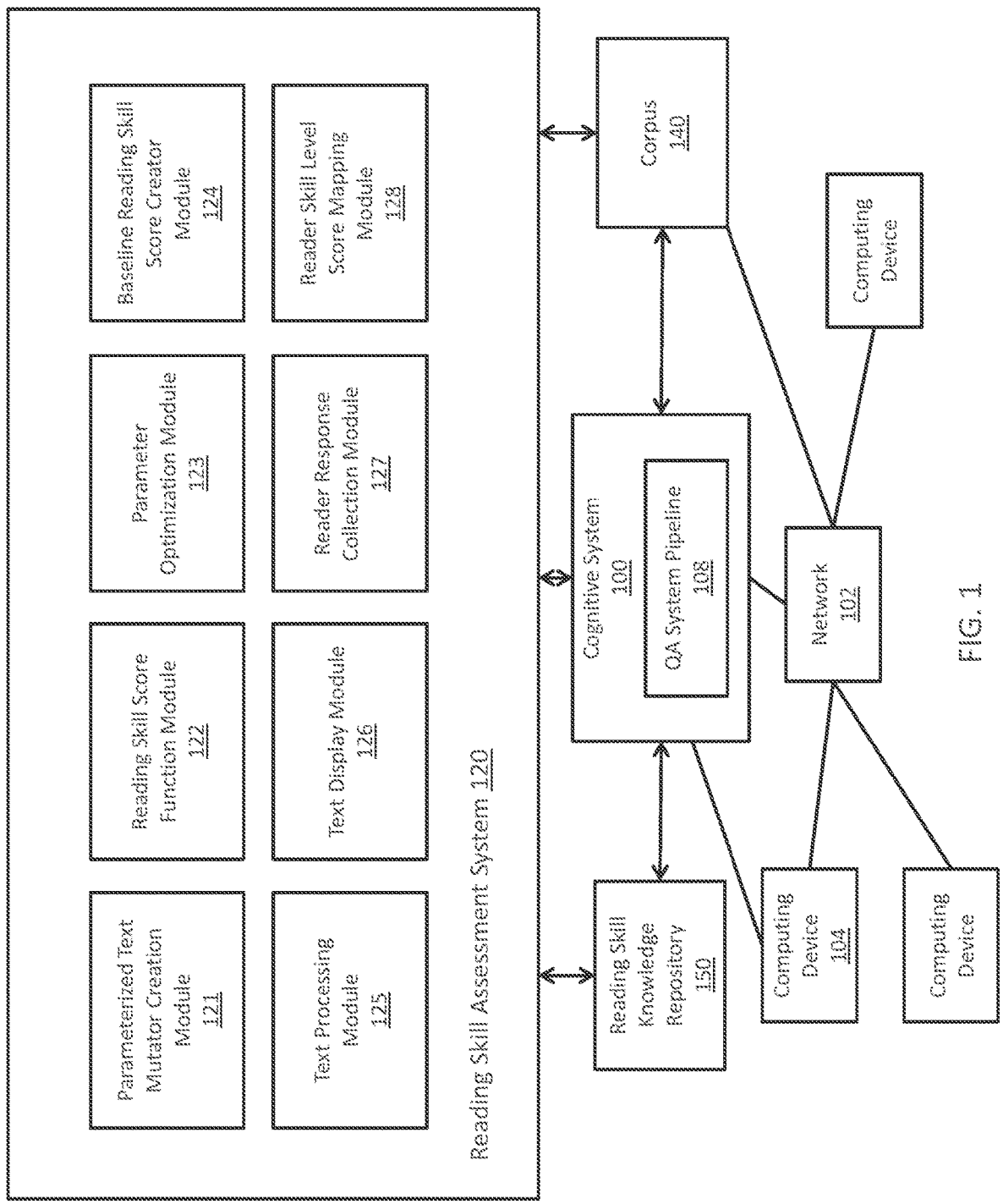
FIG. 1 depicts a schematic diagram of one illustrative embodiment of a cognitive system implementing a reading skill assessment system in a computer network.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a head disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network (LAN), a wide area network (WAN) and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operations steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. IBM Watson™ is an example of one such cognitive system which can process human readable language and identify inferences between text passages with human-like accuracy at speeds far faster than human beings and on a much larger scale. In general, such cognitive systems are able to perform the following functions:

- Navigate the complexities of human language and understanding
- Ingest and process vast amounts of structured and unstructured data
- Generate and evaluate hypotheses
- Weigh and evaluate responses that are based only on relevant evidence
- Provide situation-specific advice, insights, and guidance
- Improve knowledge and learn with each iteration and interaction through machine learning processes
- Enable decision making at the point of impact (contextual guidance)
- Scale in proportion to the task
- Extend and magnify human expertise and cognition
- Identify resonating, human-like attributes and traits from natural language
- Deduce various language specific or agnostic attributes from natural language
- High degree of relevant recollection from data points (images, text, voice) (memorization and recall)
- Predict and sense with situation awareness that mimic human cognition based on experiences
- Answer questions based on natural language and specific evidence In one aspect, cognitive systems provide mechanisms for answering questions posed to these cognitive systems using a Question Answering pipeline or system (QA system). The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area (e.g., financial domain, medical domain, legal domain, etc.) where the body of knowledge (knowledgebase) can be organized in a variety of configurations, e.g., a structured repository of domain-specific information, such as ontologies, or unstructured data related to the domain, or a collection of natural language documents about the domain.

The reading skill assessment system can introduce generic and effective reading skill evaluations suitable for a diverse audience of readers. The system can be based on parameterized text mutations rules that can be established during a reading skill assessment system learning mode for different reading skill levels. The reading skill levels can include commonly-used literacy levels, such as, but not limited to: illiterate, literate, ex-literate, experienced reader, as well as levels associated with various learning disorders and neurological impairments. The system can automatically adjust test text using parameterized mutations rules, and can then identify levels of reading ability and understanding based on calculating reading scores or metrics and matching them with predefined reading skills scores.

The system can be used for original evaluation of reading skill level, as well as for tracking the progress during the continuing process of improving reading skills. Additionally, the system can test the reading skills level of persons of all ages who may have reading abnormalities and difficulties. The system can perform an assessment of reading level and can provide reading material recommendations for expanding or improving a person's reading skill level. In an embodiment, the system can transform a text document into a format that is most suitable for the reader's level and ability to process the information by applying one or more text mutators. The system can be language independent.

A person's reading skill level can be identified by matching text reading result scores with patterns collected by processing inputs from various readers' levels during a reading skill assessment system learning mode. During system implementation, the reading skill assessment system can abstract various layers of communication between the system modules and the system's users, which can make the system extensible and open to new findings, research, and statistical data inputs and updates.

The reading skill assessment system described herein improves existing systems for assessing reading skill level by generating mutated text data with application of different mutators and evaluating a reader's feedback on the text acceptance level. Association between a set of mutators and the text acceptance levels and reading skills can be established during a system learning mode. During the reading skill assessment system runtime mode, the set of acceptance text mutators can be applied to establish a text presentation format, then the set of text of transformation mutators can applied to collect the reader's response for evaluating the reader's reading skills and comprehension level. Machine Learning classification algorithms can be applied by the system such that it can learn scoring function weights during the system learning mode.

An example use of the reading skill assessment system can be where a reader has symptoms of dyslexia, which is an educational diagnosis that describes an unexpected difficulty with reading. A dysmetric dyslexic child is unable to properly perform sequential scanning of words. To aid, the system can assemble a desired text as a set of separate word-units that can be presented to the user in a static location.

An example use of the reading skill assessment system can be where a reader has a neurological impairment that can require that the text be processed letter by letter, for example, where a reader has word-form dyslexia. In many cases, the word can then be understood by the reader when there is no misspelling, and thus the system can present a desired text on a letter-by-letter basis to the reader in a static location.

An example use of the reading skill assessment system can be where a dyslexic child reads out loud but often confuses small words like "does" and "goes." Longer words like "construction" are often incorrectly identified or skipped over. Thus, after child reads a page, he is likely not able to explain what happened in the story or to answer questions about key details in the passage. Dyslexic children frequently repeat the same kind of spelling mistakes, such as reversing letters (writing "bots" instead of "dots"), or mixing up the order of letters (writing "nip" instead of "pin"). Dyslexic children often struggle to pronounce words correctly, such as saying "mawn lower" instead of "lawn mower." Because dyslexics commonly think in pictures and not using the sounds of words, dyslexics are known to have trouble with words that do not produce a mental picture, commonly known as trigger words like "the," "of" and "for."

To evaluate the child's reading skill set level the system can adapt the content presentation to the level suitable for that reader. For example, by applying a text mutator to stretch the text by incrementally increasing the distance between the words and increasing the font size, the system can accommodate the representational level requirements for the person with ocular problems. By mutating the text using increased distance between the words, as well as placing the words in a static location, the system can accommodate a reader with reading disorders such as dyslexia.

The system can apply a different set of text mutators for generating formatted text, which can be used in the process of evaluating the reading skill levels for different skill groups. For instance, displaying misspelled test vocabulary words that are common to a particular subject would likely not prevent understanding for a reader with experience in the subject. However, there exists a higher likelihood of misunderstanding for someone who is not familiar with that subject. Additionally, having misspelled concept words in a text presented to a reader with a reading disorder would not be appropriate for testing of the reading comprehension level of the reader because a person with certain cognitive disorders may have difficulties interpreting misspelled, yet otherwise familiar, words. The system can be flexible in adjusting the text presentation formats to readers of different levels by establishing a particular set of mutators applicable to a multitude of different reading skill levels.

FIG. 1 depicts a schematic diagram of one illustrative embodiment of a cognitive system 100 implementing a question and answer (QA) pipeline 108 and a reading skill assessment system 120 in a computer network 102. One example of a question/answer generation operation which may be used in conjunction with the principles described herein is described in U.S. Patent Application Publication No. 2011/0125734, which is herein incorporated by reference in its entirety. The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables reading skill assessment functionality for one or more cognitive system users via their respective computing devices. Other embodiments of the cognitive system 100 may be used with components, systems, sub-systems, and/or devices other than those that are depicted herein.

The cognitive system 100 is configured to implement a QA pipeline 108 that receive inputs from various sources.

For example, the cognitive system 100 receives input from the network 102, a corpus of electronic documents 140, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 140. Portions of the corpus of data 140 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 140 for use as part of a corpus of data with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of data 140. In an embodiment, full questions can be generated and entered into the QA system using the reading skill assessment system 120 described herein. The cognitive system 100 parses and interprets a full question via a QA pipeline 108, and provides a response containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of data 140. The QA pipeline 108 generates answers for the input question based on the processing of the input question and the corpus of data 140. In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a QA pipeline of the IBM Watson™ cognitive system receives an input question, which it then parses to extract the major features of the question, and which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson™ cognitive system then performs deep analysis on the language of the input question and the language used in each of the portions of the corpus of data found during the application of the queries using a variety of reasoning algorithms. The scores obtained from the various reasoning algorithms are then weighted against a statistical model that summarizes a level of confidence that the QA pipeline of the IBM Watson™ cognitive system has regarding the evidence that the potential response, i.e., candidate answer, is inferred by the question. This process is repeated for each of the candidate answers to generate a ranked listing of candidate answers which may then be presented to the user that submitted the input question, or from which a final answer is selected and presented to the user. More information about the QA pipeline of the IBM Watson™ cognitive system may be obtained, for example, from the IBM Corporation website, IBM Redbooks, and the like. For example, information about the QA pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As shown in FIG. 1, in accordance with some illustrative embodiments, the cognitive system 100 is further augmented, in accordance with the mechanisms of the illustrative embodiments, to include logic implemented in specialized hardware, software executed on hardware, or any combination of specialized hardware and software executed on hardware, for implementing a reading skill assessment system 120. As described further herein, the reading skill assessment system 120 can utilize parameterized text mutator creation module 121, a reading skill score function module 122, a parameter optimization module 123, a baseline reading skill score creation module 124, a text processing module 125, a text display module 126, a reader response collection module 127, and a reader skill level score mapping module 128 to accomplish the overall function of the reading skill assessment system 120, as described further herein.

Figure 2:
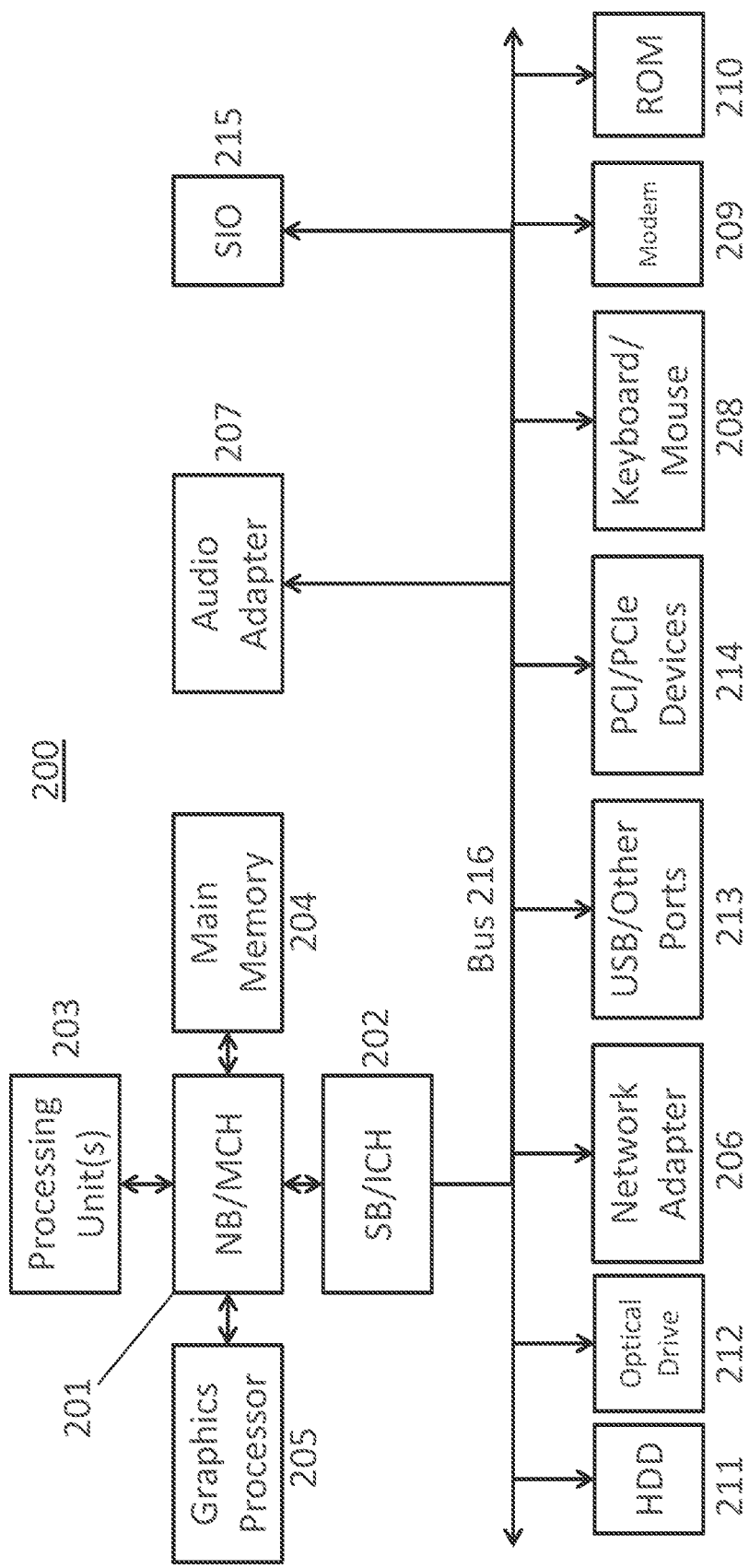
FIG. 2 is a block diagram of an example data processing system in which aspects of the illustrative embodiments may be implemented.

FIG. 2 is a block diagram of an example data processing system 200 in which aspects of the illustrative embodiments are implemented. Data processing system 200 is an example of a computer, such as a server or client, in which computer usable code or instructions implementing the process for illustrative embodiments of the present invention are located. In one embodiment, FIG. 2 represents a server computing device, such as a server, which implements the reading skill assessment system 120 and cognitive system 100 described herein.

In the depicted example, data processing system 200 can employ a hub architecture including a north bridge and memory controller hub (NB/MCH) 201 and south bridge and input/output (I/O) controller hub (SB/ICH) 202. Processing unit 203, main memory 204, and graphics processor 205 can be connected to the NB/MCH 201. Graphics processor 205 can be connected to the NB/MCH through an accelerated graphics port (AGP).

In the depicted example, the network adapter 206 connects to the SB/ICH 202. The audio adapter 207, keyboard and mouse adapter 208, modem 209, read only memory (ROM) 210, hard disk drive (HDD) 211, optical drive (CD or DVD) 212, universal serial bus (USB) ports and other communication ports 213, and the PCI/PCIe devices 214 can connect to the SB/ICH 202 through bus system 216. PCI/PCIe devices 214 may include Ethernet adapters, add-in cards, and PC cards for notebook computers. ROM 210 may be, for example, a flash basic input/output system (BIOS). The HDD 211 and optical drive 212 can use an integrated drive electronics (IDE) or serial advanced technology attachment (SATA) interface. The super I/O (SIO) device 215 can be connected to the SB/ICH.

An operating system can run on processing unit 203. The operating system can coordinate and provide control of various components within the data processing system 200. As a client, the operating system can be a commercially available operating system. An object-oriented programming system, such as the Java™ programming system, may run in conjunction with the operating system and provide calls to the operating system from the object-oriented programs or applications executing on the data processing system 200. As a server, the data processing system 200 can be an IBM® eServer System p® running the Advanced Interactive Executive operating system or the Linux operating system. The data processing system 200 can be a symmetric multiprocessor (SMP) system that can include a plurality of processors in the processing unit 203. Alternatively, a single processor system may be employed.

Instructions for the operating system, the object-oriented programming system, and applications or programs are located on storage devices, such as the HDD 211, and are loaded into the main memory 204 for execution by the processing unit 203. The processes for embodiments of the reading skill assessment system can be performed by the processing unit 203 using computer usable program code, which can be located in a memory such as, for example, main memory 204, ROM 210, or in one or more peripheral devices.

A bus system 216 can be comprised of one or more busses. The bus system 216 can be implemented using any type of communication fabric or architecture that can provide for a transfer of data between different components or devices attached to the fabric or architecture. A communication unit such as the modem 209 or network adapter 206 can include one or more devices that can be used to transmit and receive data.

Those of ordinary skill in the art will appreciate that the hardware depicted in FIG. 2 may vary depending on the implementation. Other internal hardware or peripheral devices, such as flash memory, equivalent non-volatile memory, or optical disk drives may be used in addition to or in place of the hardware depicted. Moreover, the data processing system 200 can take the form of any of a number of different data processing systems, including but not limited to, client computing devices, server computing devices, tablet computers, laptop computers, telephone or other communication devices, personal digital assistants, and the like. Essentially, data processing system 200 can be any known or later developed data processing system without architectural limitation.

Figure 3:
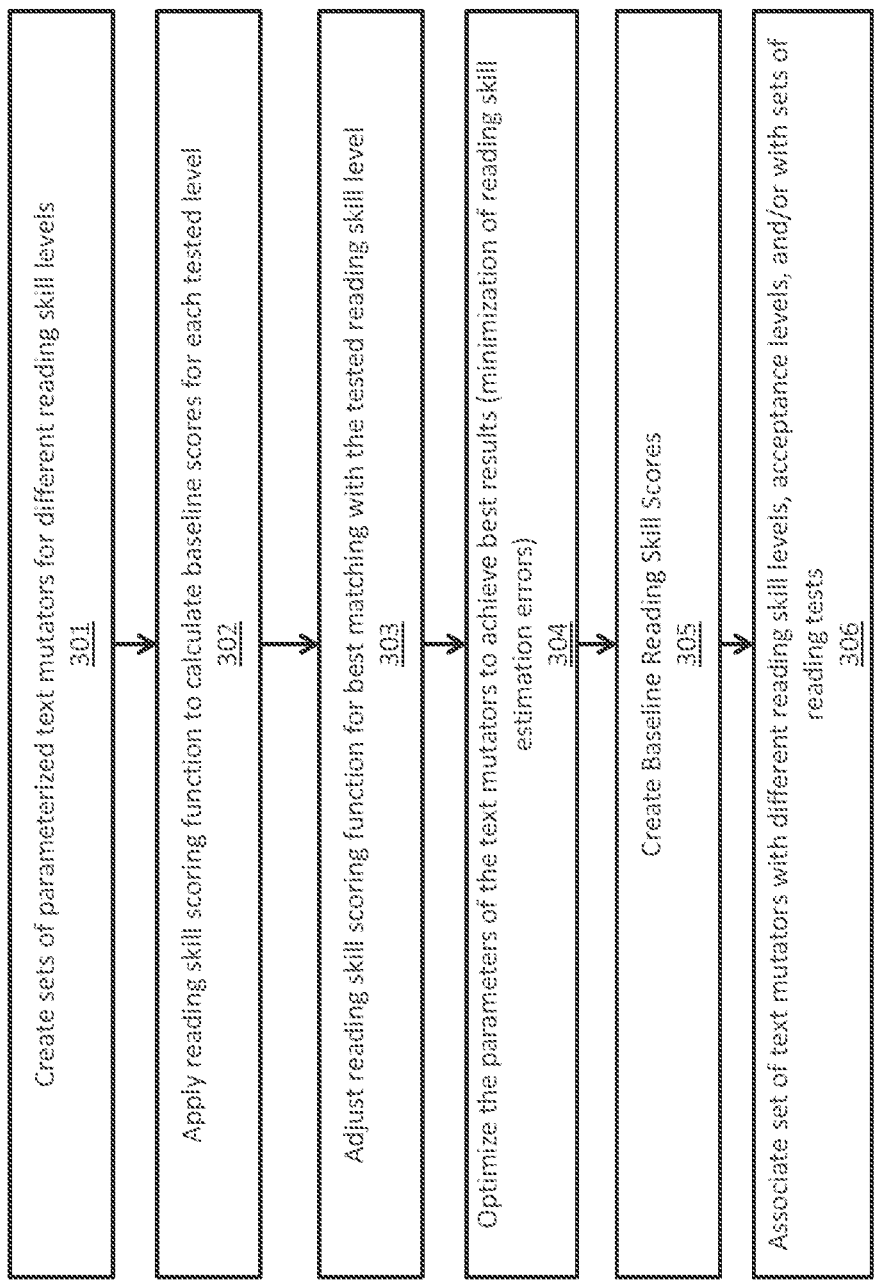
FIG. 3 depicts a flowchart illustrating the functionality of a learning mode of a reading skill assessment system, in accordance with embodiments described herein.

FIG. 3 depicts a flowchart illustrating the functionality of a learning mode of a reading skill assessment system, in accordance with embodiments described herein. During learning mode, the reading assessment system can collect data and optimize the reading skill evaluation model. The system can begin by creating one or more sets of parameterized text mutators for different reading skill levels 301 by utilizing the parameterized text mutator creation module 121 (as shown in FIG. 1). The reading skill levels can include commonly-used literacy levels, such as, but not limited to: illiterate, literate, ex-literate, experienced reader, as well as levels associated with various learning disorders and neurological impairment. Text mutators are described in more detail in FIG. 5, and include, but are not limited to: pseudoword injections, letter transposition injections, randomized text, word rotation, mirroring, letter spacing, word extraction, and text stretching.

The system can then apply a reading skill score function, using the reading skill score function module 122 (as shown in FIG. 1) to calculate baseline scores for each tested level 302. The reading skill score function can then be adjusted for best matching with the tested reading skill level 303. Subsequently, the system can optimize the parameters of the text mutators, using the parameter optimization module 123 (as shown in FIG. 1) to achieve the best results 304, which can be defined as leading to the results that can lead to the highest minimization of reading skill level estimation errors. The system can then proceed to calculate baseline reading skill scores 305, using the baseline reading skill score creator module 124 (as shown in FIG. 1). Finally, the system can associate one or more sets of text mutators with different reading skill levels, acceptance levels, and/or with one or more sets of reading tests 306. The baseline reading skill scores and skill score level associations can be stored by the system in a reading skill knowledge repository 150.

Figure 4:
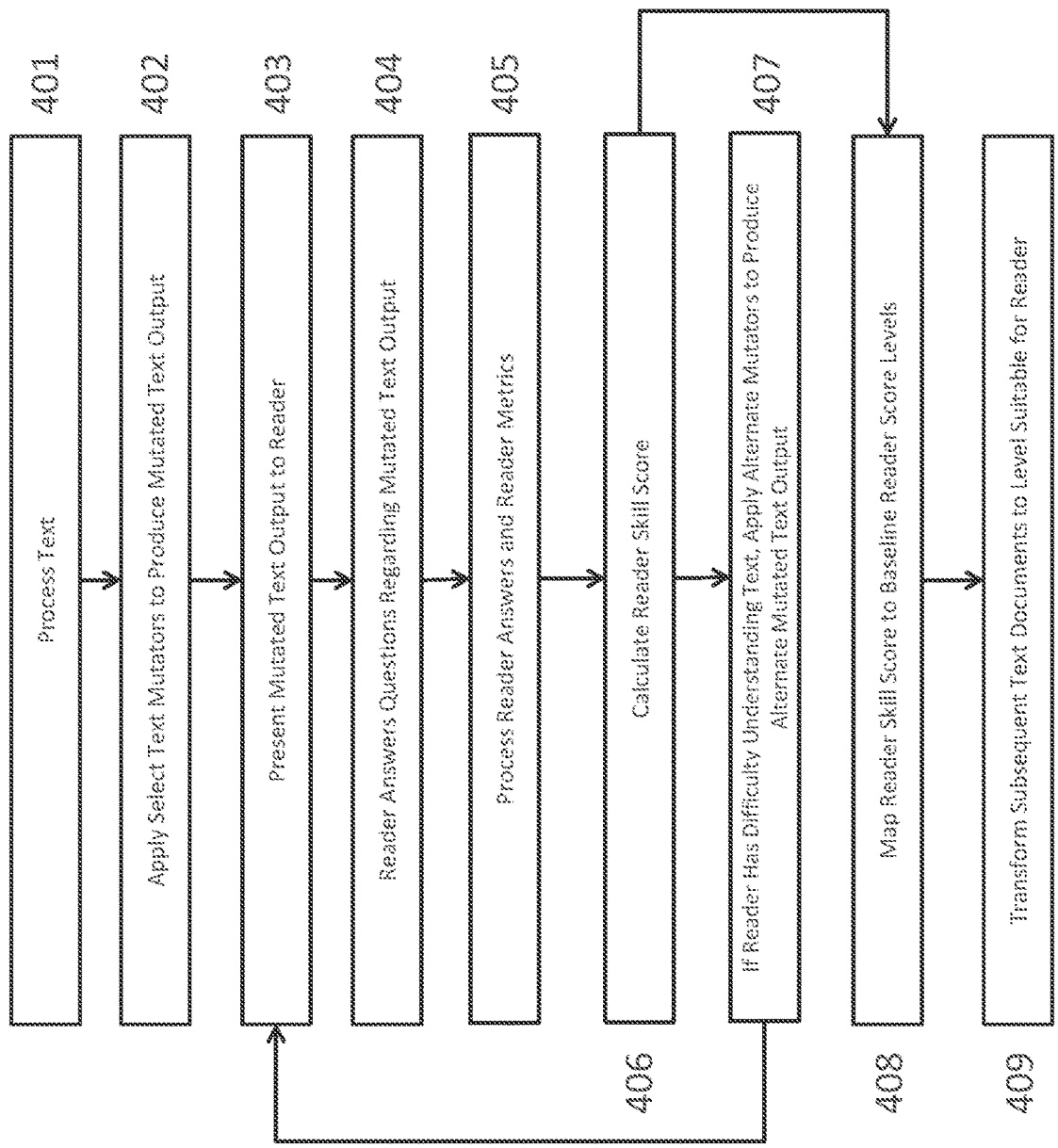
FIG. 4 depicts a flowchart illustrating the functionality of a runtime mode of a reading skill assessment system, in accordance with embodiments described herein.

The reading score function can input all reader metrics (as described in FIG. 6) and can calculate the reader reading skill levels during runtime mode (as described in FIG. 4). During learning mode, the reading score function can be parameterized and optimized. The more data the system collects, the more accurate the reading score function output. If the system has accumulated substantial data, standard machine learning techniques can be applied to calculate the function parameters.

An example reading score function can be described using the following formula: $F=\Sigma(weight*metric)+\theta(text\ difficulty)$. By introducing text difficulty the system can compare text content with baseline text suitable for a particular age group. In so doing, the function can be flexible and adaptable to the text with various complexity levels. Weights (parameters) of the reading scoring function can be calculated by applying machine learning classification algorithms during the system learning mode.

FIG. 4 depicts a flowchart illustrating the functionality of a runtime mode of a reading skill assessment system, in accordance with embodiments described herein. First, the system can process a body of text 401 using a text processing module 125 (as shown in FIG. 1). Processing of the text can involve extraction and parsing of all words in the text, as well as identification of sentence, paragraphs, and other section structures. The system can then apply one or more select text mutators to the body of text in order to produce a mutated text output 402 or can not apply any text mutators. The mutated text output can then be presented to a reader 403 using a text display module 126 (as shown in FIG. 1). After the reader reads the mutated text output, the system can then prompt the reader with a series of questions, and the reader can answer the one or more questions regarding the mutated text output 404, where the answers can be collected by the system using a reader response collection module 127 (as shown in FIG. 1).

The system can then process the reader's answers to the series of questions, as well as process the reader's metrics (as described in FIG. 6), which can be collected while the reader is answering the one or more questions regarding the mutated text output 405. The system can then calculate a reader skill score for the reader 406. After processing, if it is established that the reader had difficultly reading the mutated text output, the system can apply an alternate set of text mutators to produce an alternate mutated text output 407. In an embodiment, the alternate set of text mutators can match the lower reading level of the reader. The system can then repeat the presentation step 403, question answering step 404, and collection step 405. If, after the original mutated text output or the alternate mutated text output is read, the system processes that the text has been understood, the system can use the calculated reader skill score values and map those score values to the baseline reader score levels 408 using a reader skill level score mapping module 128 (as shown in FIG. 1). In an embodiment, the system can transform one or more subsequent text documents into a format that is most suitable for the reader's level and ability to process the information using one or more of the text mutators 409.

Figure 5:
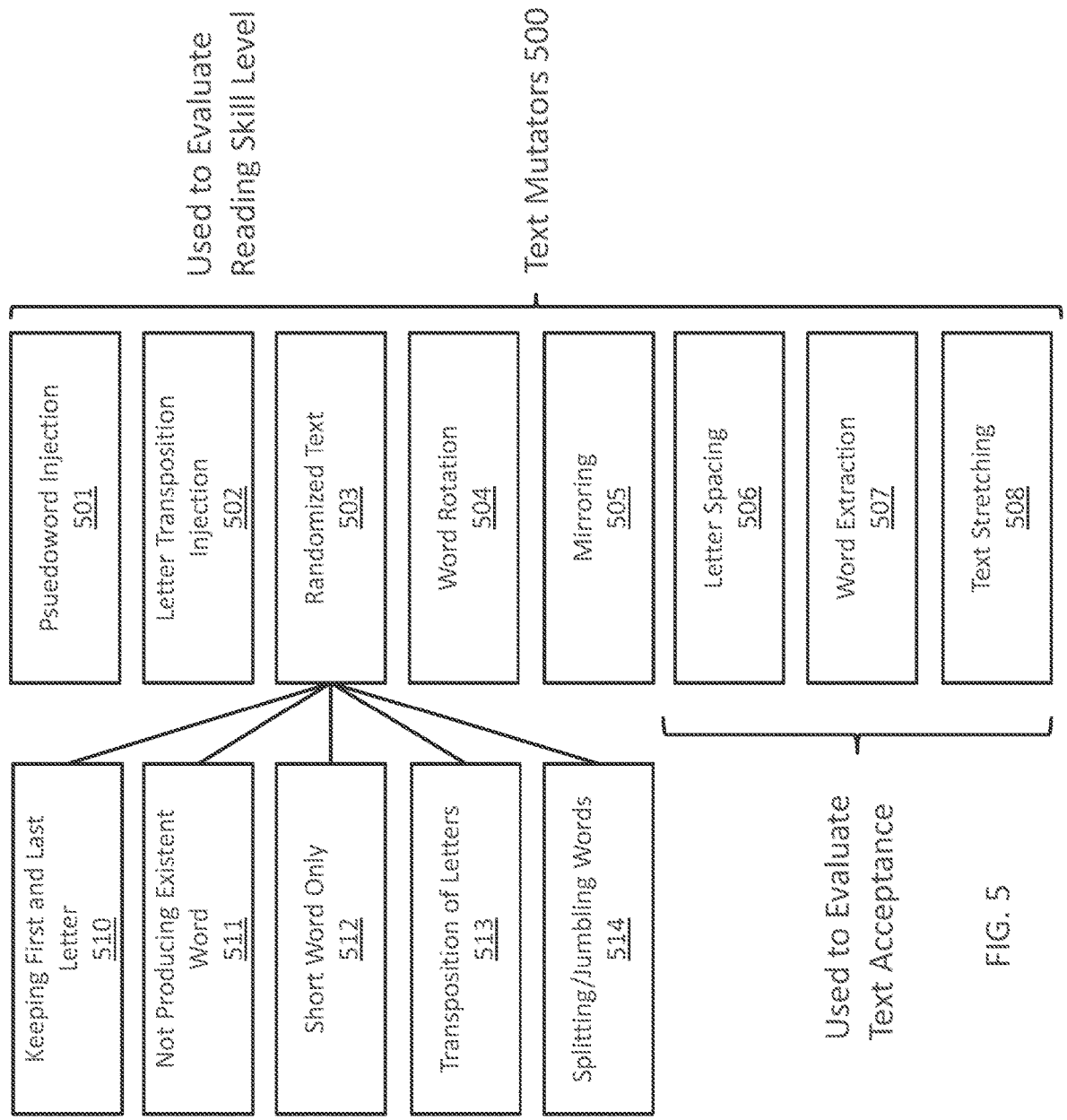
FIG. 5 depicts a block diagram illustrating text mutators that can be used by the reading skill assessment system, according to embodiments described herein.

FIG. 5 depicts a block diagram illustrating text mutators 500 that can be used by the reading skill assessment system, according to embodiments described herein. Text mutators 500 can include, but are not limited to: pseudoword injections 501, letter transposition injections 502, randomized text 503, word rotation 504, mirroring 505, letter spacing 506, word extraction 507, and text stretching 508. All mutators can be used to evaluate reading skill level. However, letter spacing 506, word extraction 507, and text stretching 508 can be used to text acceptance levels.

Psuedoword injection 501 can involve inserting one or more psuedoword into particular test text section. A psuedoword can be a unit of speech or text that appears to an actual meaningful word in a particular language, but in fact does not have any meaning in the current lexicon.

Letter transpositions 502 can involve injecting one or more words into a test text section which can be generated by letter transposition (moving around and/or replacement of letters), while still preserving the original sound or pronunciation of the word (i.e., misspelling text).

Randomized text 503 can involve the insertion into or replacement of test text with randomized words generated according to one or more randomization rules. Randomization rules can include, but are not limited to: keeping the first and last letter of the word, but jumbling all letters in-between 510; not producing existent words (i.e., producing a nonsense phrase) 511; producing short words only 512; transposing one or more letters of text, either adjacent ("suolution" instead of "solution") or further apart ("soutulion" instead of "solution") 513; and splitting words and/or jumbling the spelling of those splittings 514.

Word rotation 504 can involve the rotation of either the orientation of the entire word, or a rotation of the letters within the word. In an embodiment, the rotation can be consistent across all words and/or letters. In an alternate embodiment, the rotation degree can be variable between words and/or letters.

Mirroring 505 can involve displaying one or more words as if they were reflected in a mirror. In an embodiment, mirroring 505 can involve the rotation of one or more letters along an axis defined as the underline of the particular word. For example, "mirror" can be displayed as "w! ʀʀoʀ " In an alternate embodiment, the letters of a mirrored word can be rotated along an axis defined in the center point of each letter. For example, "mirror" can be displayed as " miɲoɿ ." In an alternate embodiment, mirroring 505 can involve rotating the entire word along an axis defined against the right edge of the last letter of the word. For example, "mirror" can be displayed as "ɿoɲɿim."

Letter spacing 506 can involve varying the spacing between the letters of a particular word or set of words. In an embodiment, the spacing between letters can be consistently varied, while in an alternate embodiment, the letter spacing can be inconsistently varied between adjacent sets of letters.

Word extraction 507 can involve removing one or more words from a particular test text. In an embodiment, word extraction 507 can involve redisplaying a particular test text word by word, where the words are sequentially displayed one at a time in a single display area. Thus, word extraction 507 can remove the overall sentence structure of the test text, or can be used to remove particular words, such as vocabulary words, and present them on a word-by-word basis to a reader.

Stretching text 508 can involve altering both the distance between adjacent letters, as well as altering the dimensions of a particular letter, either in a vertical or a horizontal direction, while keeping the other direction unaltered. In other words, text can be stretched to increase its width and/or its height.

Figure 6:
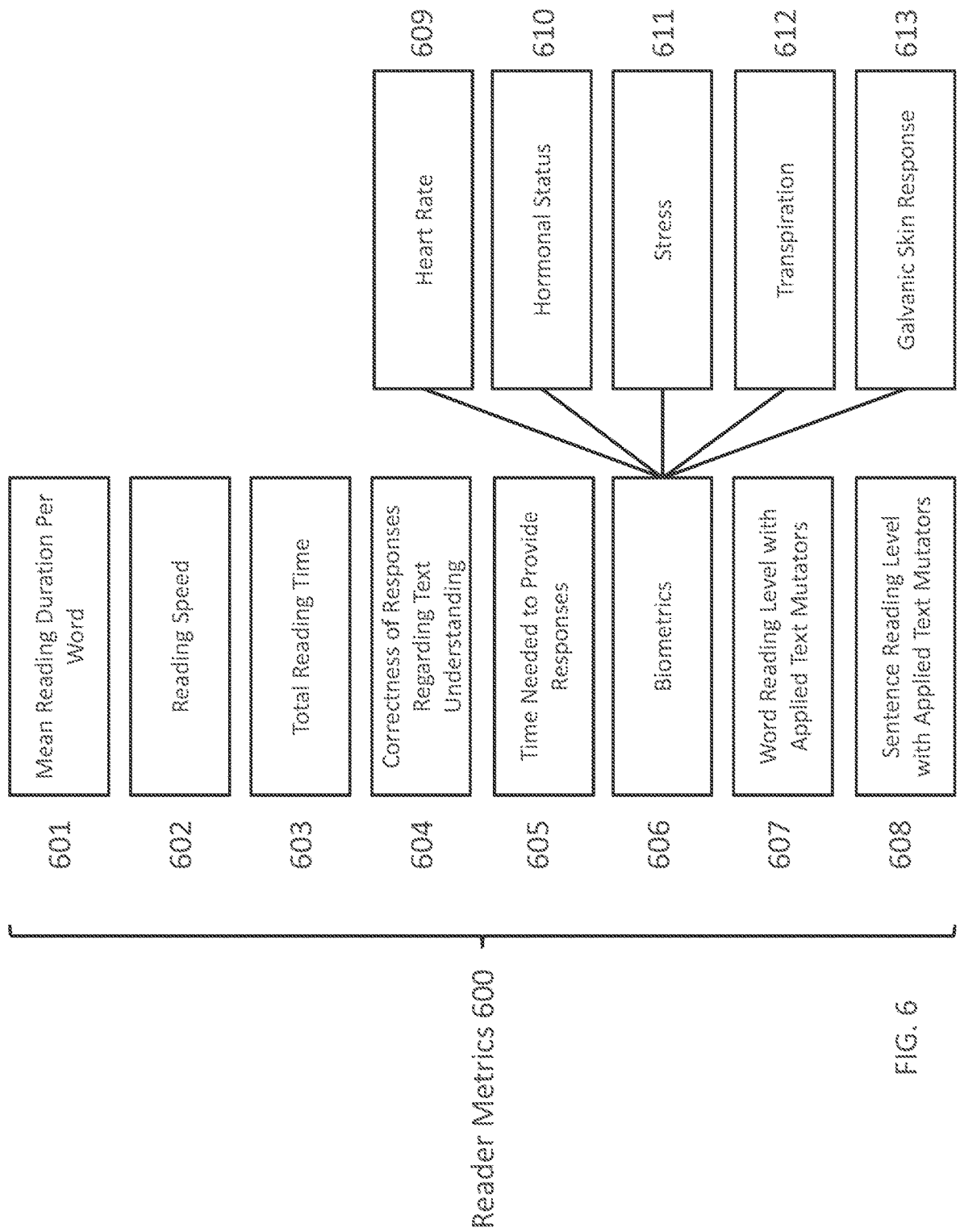
FIG. 6 depicts a block diagram illustrating reader metrics that can be collected by the reading skill assessment system, according to embodiments described herein.

FIG. 6 depicts a block diagram illustrating reader metrics 600 that can be collected by the reading skill assessment system, according to embodiments described herein. Reader metrics 600 can include, but are not limited to: mean reading duration per word 601, reading speed 602, total reading time 603, correctness of responses regarding text understanding 604, time needed to provide responses 605, biometrics 606, word reading level with applied text mutators 607, and sentence reading level with applied mutators 608.

Mean reading duration per word 601 can be measured by taking the average of the reading speed, which can be measured as words per minute or other time frame, which can itself be derived by diving the total reading time 603, which can be measured as a function of time, by the number of words in the sample of test text presented to the reader.

Correctness of responses regarding text understanding 604 can be measured by determining the number of correct answers as relate to context driven questions presented to the reader regarding the subject of the text, also known as reading comprehension questions. Excluded questions can include word identification or basic spelling questions, which do not directly relate to identifying whether or not the reader actually understood what the sample of test text actually means.

Time needed to provide responses 605 can be measured per question, or can be added up to determine the total time needed for the reader to respond to all questions provided by the system after the mutated output text or original text is provided to the reader.

Biometrics 606 can be measured during all phases of reader operation of the reading skill level assessment system. Biometrics 606 that can be measured by the system can include, but are not limited to: heart rate 609, hormonal status 610, stress levels 611, transpiration 612, and galvanic skin response 613.

Word reading level with applied text mutators 607 and sentence reading level with applied text mutators 608 can be measured when mutated output text or alternate mutated output text is provided to the reader, and can be of particular use in determining whether or not the reader has a reading difficulty or other cognitive impairment that affects reading.

To illustrate an example of the functionality of the learning mode and the runtime mode of the reading skill assessment system, the system can be assigned to evaluate reading skills using biology as a designated subject. A body of testing text can comprise the paragraph: "Individuals that are poorly adapted to their environment are less likely to survive and reproduce. You need to remember that variation can be caused by both genes and the environment. But it is only variation caused by genes that can be passed on to the next generation."

As described in the example, vocabulary test words can include "variation" and "genes." Reading skill levels can be defined numerically on a scale of 1-10, which can translate into a set of example categories of readers having an age between 12 and 14 years: 1) experienced readers who can have an understanding of the biological concept of "variation" and "genes," (level 10); 2) less experienced readers who can comprehend the test text but are not familiar with the biological concepts of "variation" and/or "genes, (level 8-9); 3) readers with developed reading difficulties, such as dyslexia, familiar with words such as "variation" and/or "genes," but who can otherwise have difficulty in reading the test text (level 6); 4) readers with developed dyslexia, unfamiliar with words such as "variation" and/or "genes," and who also have difficulty in reading the text (level 3); and readers with ocular problems, and are totally unfamiliar with biological subject concept (level 7).

As part of evaluating the reading skill levels, the system can apply text mutators including: a) pseudoword injection; b) text stretching; c) letter transposition injection; and d) word extraction. In learning mode, the system can create five test scenarios using the test text and the text mutators. Test 1 can involve display of the non-modified text and the collection of reader metrics including total reading time, reading speed, time needed to provide responses, and correctness of responses regarding text understanding. Test 2 can involve display of modified text using psuedoword injection to replace vocabulary words and the collection of reader metrics including total reading time, reading speed, time needed to provide responses, and correctness of responses regarding text understanding. Test 3 can involve display of modified text using text stretching and collection of the reader metrics including total reading time and reading speed. Test 4 can involve display of modified text using letter transposition injection and the collection of reader metrics including total reading time, reading speed, time needed to provide responses, and correctness of responses regarding text understanding. Test 5 can involve display of modified text using word extraction of the vocabulary words and the collection of reader metrics including total reading time, reading speed, time needed to provide responses, and correctness of responses regarding text understanding.

Values for reading skills can be calculated by the reading score function. An average within each selected testing group (1-5) can be calculated. In an embodiment, metrics values can be normalized in a 0-1 range. By applying machine learning processes, the reading score level training can be performed within multiple iterations by adjusting the weights applied for each metric in order to minimize the error of the reading score function.

During the system runtime mode, the learned reading score levels can be applied to the baseline tests results for calculating reading scores. By matching reading scores with the baselines results, a suggested reading skill level can be suggested for the tested reader.

The present description and claims may make use of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

The system and processes of the figures are not exclusive. Other systems, processes and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A computer implemented method, in a data processing system comprising a processor and a memory comprising instructions which are executed by the processor to cause the processor to implement a reading skill assessment system on a cognitive system, the method comprising:
    processing a body of text in a learning mode;
    applying one or more text mutators to the body of text to produce a mutated text output based on a plurality of randomization rules, wherein the plurality of randomization rules further comprises: keeping a first letter and a last letter of a particular word while jumbling all letters between the first letter and the last letter of the particular word; transposing one or more letters of text; splitting words; and jumbling a spelling of a split word;
    presenting the mutated text output to a reader;
    prompting the reader to provide one or more answers to one or more questions through the cognitive system regarding the mutated text output;
    processing the one or more answers provided by the reader;
    processing one or more metrics collected from the reader, wherein the one or more metrics include biometrics and one or more of mean reading duration per word, reading speed, total reading time, correctness of responses regarding text understanding, time needed to provide responses, word reading level with applied text mutators, and sentence reading level with applied text mutators; wherein the biometrics includes one or more of heart rate, hormonal status, stress levels, transpiration, and galvanic skin response;
    calculating a reader skill score for the reader based on the collected metrics, wherein one or more machine learning classification algorithms are applied to learn at least one parameter of a scoring function of the reader skill score;
    mapping the calculated reader skill score against one or more baseline reading skill score levels; and
    suggesting a reading skill level to the reader.

2. The method as recited in claim 1, further comprising:
    processing one or more metrics collected from the reader, wherein the metrics collected comprise at least one of: mean reading duration per word, reading speed, total reading time, correctness of responses regarding text understanding, time needed to provide responses, biometrics, word reading level with applied text mutators, and sentence reading level with applied mutators.

3. The method as recited in claim 1, further comprising:
    determining whether the reader had difficulty reading the mutated text output based upon the one or more answers received and one or more metrics collected;
    if the reader had difficulty reading the mutated text output:
        applying an alternate set of text mutators to produce an alternate mutated text output;
        presenting the alternate mutated text output to a reader;
        prompting the reader to provide one or more answers to one or more questions regarding the alternate mutated text output;
        processing the one or more answers provided by the reader;
        processing one or more metrics collected from the reader;
        calculating a reader skill score for the reader; and
        mapping the calculated reader skill score against one or more baseline reading skill score levels.

4. The method as recited in claim 1, further comprising:
    transforming one or more subsequent text documents into a format suitable for the reader's suggested reading skill level by applying one or more of the text mutators to the subsequent text documents.

5. The method as recited in claim 1, further comprising:
    deriving the one or more baseline reading skill score levels by:
        creating the one or more sets of parameterized text mutators for one or more different reading skill levels;
        applying a reading skill score function to calculate baseline scores for one or more tested reading skill levels;
        adjusting the reading skill score function to best match with the one or more tested reading skill levels;
        optimizing the parameters of the one or more sets of text mutators;
        creating the one or more baseline reading skill score levels for each of the one or more tested reading skill levels; and
        associating one or more sets of text mutators with the one or more tested reading skill levels.

6. A computer program product for reading skill assessment implemented on a cognitive system, the computer program product comprising a computer readable storage medium having program instructions embodied therewith, the program instructions executable by a processor to cause the processor to:
    process a body of text in a learning mode;
    apply one or more text mutators to the body of text to produce a mutated text output based on a plurality of randomization rules, wherein the plurality of randomization rules further comprises: keeping a first letter and a last letter of a particular word while jumbling all letters between the first letter and the last letter of the particular word; transposing one or more letters of text; splitting words; and jumbling a spelling of a split word;
present the mutated text output to a reader;
prompt the reader to provide one or more answers to one or more questions through the cognitive system regarding the mutated text output;
process the one or more answers provided by the reader;
process one or more metrics collected from the reader, wherein the one or more metrics include biometrics and one or more of mean reading duration per word, reading speed, total reading time, correctness of responses regarding text understanding, time needed to provide responses, word reading level with applied text mutators, and sentence reading level with applied text mutators; wherein the biometrics includes one or more of heart rate, hormonal status, stress levels, transpiration, and galvanic skin response;
calculate a reader skill score for the reader based on the collected metrics, wherein one or more machine learning classification algorithms are applied to learn at least one parameter of a scoring function of the reader skill score;
map the calculated reader skill score against one or more baseline reading skill score levels; and
suggest a reading skill level to the reader.

7. The computer program product as recited in claim 6, wherein the processor is further caused to:
process one or more metrics collected from the reader, wherein the metrics collected comprise at least one of: mean reading duration per word, reading speed, total reading time, correctness of responses regarding text understanding, time needed to provide responses, biometrics, word reading level with applied text mutators, and sentence reading level with applied mutators.

8. The computer program product as recited in claim 6, wherein the processor is further caused to:
determine whether the reader had difficulty reading the mutated text output based upon the one or more answers received and one or more metrics collected;
if the reader had difficulty reading the mutated text output:
apply an alternate set of text mutators to produce an alternate mutated text output;
present the alternate mutated text output to a reader;
prompt the reader to provide one or more answers to one or more questions regarding the alternate mutated text output;
process the one or more answers provided by the reader;
process one or more metrics collected from the reader;
calculate a reader skill score for the reader; and
map the calculated reader skill score against one or more baseline reading skill score levels.

9. The computer program product as recited in claim 6, wherein the processor is further caused to:
transform one or more subsequent text documents into a format suitable for the reader's suggested reading skill level by applying one or more of the text mutators to the subsequent text documents.

10. The computer program product as recited in claim 6, wherein the processor is further caused to:
derive the one or more baseline reading skill score levels by:
creating the one or more sets of parameterized text mutators for one or more different reading skill levels;
applying a reading skill score function to calculate baseline scores for one or more tested reading skill levels;
adjusting the reading skill score function to best match with the one or more tested reading skill levels;
optimizing the parameters of the one or more sets of text mutators;
creating the one or more baseline reading skill score levels for each of the one or more tested reading skill levels; and
associating one or more sets of text mutators with the one or more tested reading skill levels.

11. A reading skill assessment system implemented on a cognitive system, comprising:
a reading skill assessment processor configured to:
process a body of text in a learning mode;
apply one or more text mutators to the body of text to produce a mutated text output based on a plurality of randomization rules, wherein the plurality of randomization rules further comprises: keeping a first letter and a last letter of a particular word while jumbling all letters between the first letter and the last letter of the particular word; transposing one or more letters of text; splitting words; and jumbling a spelling of a split word;
present the mutated text output to a reader;
prompt the reader to provide one or more answers to one or more questions through the cognitive system regarding the mutated text output;
process the one or more answers provided by the reader;
process one or more metrics collected from the reader, wherein the one or more metrics include biometrics and one or more of mean reading duration per word, reading speed, total reading time, correctness of responses regarding text understanding, time needed to provide responses, word reading level with applied text mutators, and sentence reading level with applied text mutators; wherein the biometrics includes one or more of heart rate, hormonal status, stress levels, transpiration, and galvanic skin response;
calculate a reader skill score for the reader based on the collected metrics, wherein one or more machine learning classification algorithms are applied to learn at least one parameter of a scoring function of the reader skill score;
map the calculated reader skill score against one or more baseline reading skill score levels; and
suggest a reading skill level to the reader.

12. The system as recited in claim 11, wherein the reading skill assessment processor is further configured to:
process one or more metrics collected from the reader, wherein the metrics collected comprise at least one of: mean reading duration per word, reading speed, total reading time, correctness of responses regarding text understanding, time needed to provide responses, biometrics, word reading level with applied text mutators, and sentence reading level with applied mutators.

13. The system as recited in claim 11, wherein the reading skill assessment processor is further configured to:
determine whether the reader had difficulty reading the mutated text output based upon the one or more answers received and one or more metrics collected;
if the reader had difficulty reading the mutated text output:
apply an alternate set of text mutators to produce an alternate mutated text output;

present the alternate mutated text output to a reader;
prompt the reader to provide one or more answers to one or more questions regarding the alternate mutated text output;
process the one or more answers provided by the reader;
process one or more metrics collected from the reader;
calculate a reader skill score for the reader; and
map the calculated reader skill score against one or more baseline reading skill score levels.

14. The system as recited in claim 11, wherein the reading skill assessment processor is further configured to:
transform one or more subsequent text documents into a format suitable for the reader's suggested reading skill level by applying one or more of the text mutators to the subsequent text documents.

15. The system as recited in claim 11, wherein the reading skill assessment processor is further configured to:
derive the one or more baseline reading skill score levels by:
creating the one or more sets of parameterized text mutators for one or more different reading skill levels;
applying a reading skill score function to calculate baseline scores for one or more tested reading skill levels;
adjusting the reading skill score function to best match with the one or more tested reading skill levels;
optimizing the parameters of the one or more sets of text mutators;
creating the one or more baseline reading skill score levels for each of the one or more tested reading skill levels; and
associating one or more sets of text mutators with the one or more tested reading skill levels.

* * * * *